(12) United States Patent
Wang et al.

(10) Patent No.: US 9,140,805 B2
(45) Date of Patent: Sep. 22, 2015

(54) APPARATUS AND METHOD FOR IMPROVING UNIFORMITY OF PERFORMANCE IN POSITRON EMISSION TOMOGRAPHY

(71) Applicants: Gin Chung Wang, Grayslake, IL (US); Kent C. Burr, Buffalo Grove, IL (US); Huini Du, Vernon Hills, IL (US); Jerry Wang, Lake Zurich, IL (US)

(72) Inventors: Gin Chung Wang, Grayslake, IL (US); Kent C. Burr, Buffalo Grove, IL (US); Huini Du, Vernon Hills, IL (US); Jerry Wang, Lake Zurich, IL (US)

(73) Assignees: KABUSHIKI KAISHA TOSHIBA, Tokyo (JP); TOSHIBA MEDICAL SYSTEMS CORPORATION, Otawara-shi (JP)

( * ) Notice: Subject to any disclaimer, the term of this patent is extended or adjusted under 35 U.S.C. 154(b) by 0 days.

(21) Appl. No.: 13/657,533

(22) Filed: Oct. 22, 2012

(65) Prior Publication Data

US 2014/0110589 A1    Apr. 24, 2014

(51) Int. Cl.
*G01T 1/161* (2006.01)
*G01T 1/164* (2006.01)
*G01T 1/29* (2006.01)
*A61B 6/03* (2006.01)

(52) U.S. Cl.
CPC ............. *G01T 1/1648* (2013.01); *G01T 1/2985* (2013.01); *A61B 6/037* (2013.01)

(58) Field of Classification Search
CPC ..... G01T 1/163; G01T 1/2985; G01T 1/1644; G01T 1/2018

USPC .................................................... 250/363.02
See application file for complete search history.

(56) References Cited

U.S. PATENT DOCUMENTS 8,080,780 B2 * 12/2011 Burr et al. .................. 250/252.1
2011/0301918 A1 * 12/2011 Haselman et al. ............ 702/187
2012/0267537 A1 * 10/2012 Gagnon .................... 250/363.03

FOREIGN PATENT DOCUMENTS

| JP | 10-48340 | 2/1998 |
| JP | 2006-84309 | 3/2006 |
| WO | WO 2008/102422 A1 | 8/2008 |

OTHER PUBLICATIONS

English translation of International Search Report issued Feb. 4, 2014, in PCT/JP2013/078602 (Japanese version previously filed).
International Search Report and Written Opinion issued Feb. 4, 2014 in Application No. PCT/JP2013/078602 (With English Translation of Category of Cited Documents).

* cited by examiner

*Primary Examiner* — David Porta
*Assistant Examiner* — Edwin Gunberg
(74) *Attorney, Agent, or Firm* — Oblon, McClelland, Maier & Neustadt, L.L.P.

(57) ABSTRACT

A method of arranging detector modules within a gamma ray detector apparatus, each detector module including an array of scintillation crystals to convert light into electrical signals, the light being generated in response to incident gamma rays generated by an annihilation event, the method including obtaining performance information of each of the detector modules, and determining a relative location for each of the detector modules within the gamma ray detector based on the obtained performance information of the detector modules.

10 Claims, 11 Drawing Sheets

APPARATUS AND METHOD FOR IMPROVING UNIFORMITY OF PERFORMANCE IN POSITRON EMISSION TOMOGRAPHY

FIELD

The present disclosure generally relates to an apparatus and method for improving the uniformity of performance in positron emission tomography (PET). More specifically, the present disclosure relates to an apparatus and method for improving the uniformity of performance across the field-of-view (FOV) in PET by arranging detector modules within the scanner ring based on performance information of the detector modules.

BACKGROUND

A PET system is conventionally made of tens to about a hundred detector modules with different timing properties. Conventionally, detector modules are randomly arranged within a PET scanner. For example, for a PET detector having a plurality of detector modules arranged to form the detector ring, the detector modules are typically randomly arranged within the detector ring.

For a time-of-flight (TOF) PET scanner, this randomness usually results in a non-uniform timing resolution in the PET FOV and in the image plane. When modeled appropriately, this non-uniformity makes image reconstruction more complicated, and when not addressed, it deteriorates the image quality.

BRIEF DESCRIPTION OF THE DRAWINGS

A more complete appreciation of the embodiments described herein, and many of the attendant advantages thereof will be readily obtained as the same becomes better understood by reference to the following detailed description when considered in connection with the accompanying drawings, wherein.

DETAILED DESCRIPTION

Figure 1:
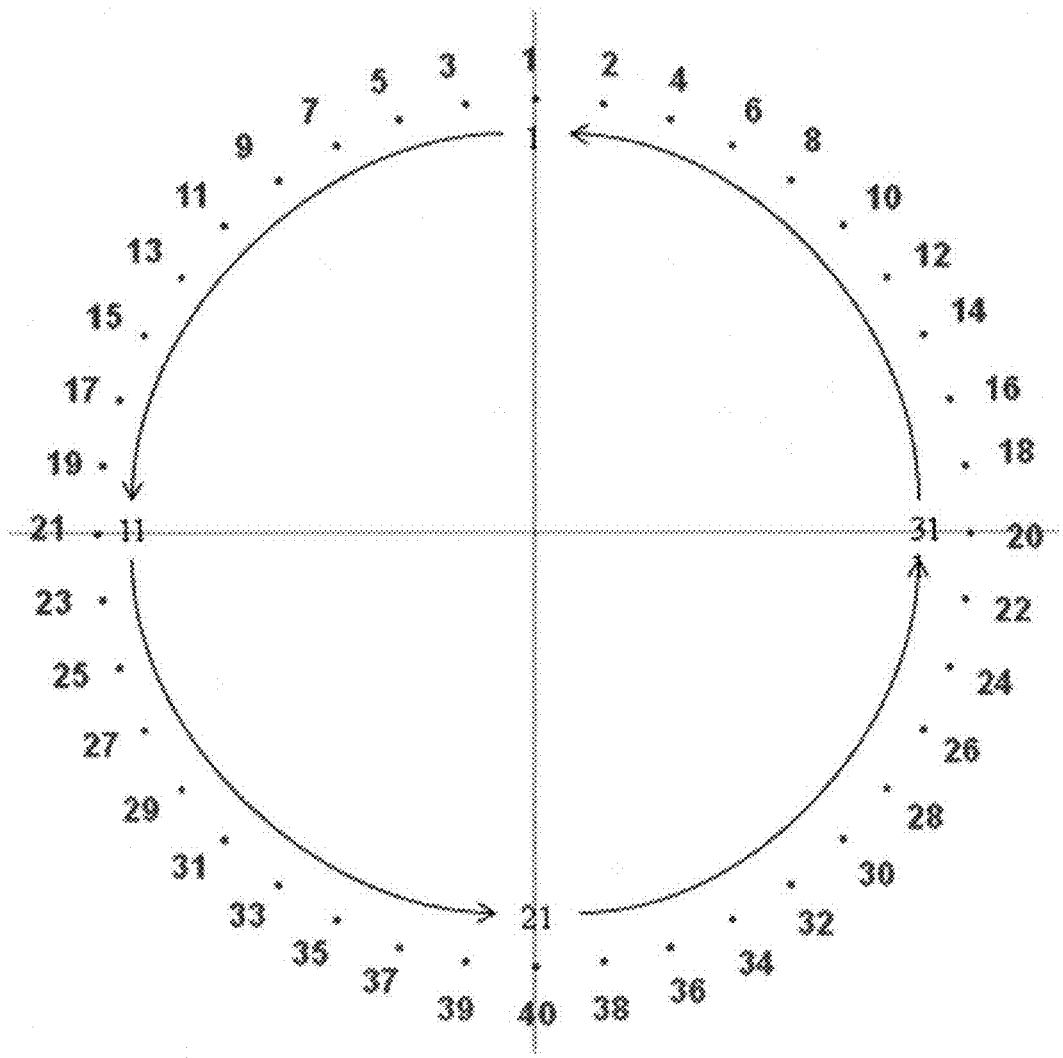
FIG. 1 shows an example arrangement of 40 detector modules within the scanner ring of a PET scanner.

The present disclosure describes an apparatus and method for improving the uniformity of performance in a PET scanner, and more specifically, an apparatus and method for improving the uniformity of performance across the FOV in a PET scanner by arranging detector modules within a scanner ring based on performance information of the detector modules.

Embodiments disclosed herein provide a method to arrange the detector modules in a PET scanner using prior information, e.g., preliminary and/or production performance characteristics of the detector modules, to equalize their timing resolutions, leading to a more uniform timing resolution across the PET scanner. The benefit of improving image quality by using TOF information is also achieved over the FOV.

According to one embodiment, a method is provided for arranging detector modules within a gamma ray detector apparatus, each detector module including an array of scintillation crystals to convert light into electrical signals, the light being generated in response to incident gamma rays generated by an annihilation event, the method including obtaining performance information of each of the detector modules, and determining a relative location for each of the detector modules within the gamma ray detector based on the obtained performance information of the detector modules.

According to one embodiment, a gamma ray detector apparatus is provided that includes a plurality of detector modules arranged to form a detector ring, each detector module including an array of scintillation crystals to convert light into an electrical signal, the light being generated in response to incident gamma rays generated by an annihilation event, wherein the detector modules are arranged within the detector ring based on a performance property of the detector modules.

According to one embodiment, a method is provided to measure the timing resolution of each detector module and to rank the detector modules in a PET scanner based on their timing resolutions.

According to one embodiment, the detector modules are paired such that the average timing resolution of each pair is as close to the same as possible. The detector modules belonging to a pair are then arranged within a PET scanner such that their locations are the mirror of each other with respect to the center of the FOV.

According to one embodiment, the detector modules are arranged so that any detector module with a relatively low timing performance has a low probability of being paired with another detector module with a relatively low timing performance.

According to one embodiment, an algorithm is used to consider the line-of-responses (LORs) from the detector modules to optimize the timing resolution uniformity.

According to one embodiment, the detector modules are arranged such that an object organ (e.g. the heart) is located in a region with relatively better timing resolution.

According to one embodiment, a method is provided to equalize timing resolution in a PET scanner by coupling a detector module with relatively good timing resolution with readout electronics with relatively poor timing performance.

Referring now to the drawings, wherein like reference numerals designate identical or corresponding parts throughout the several views, FIG. 1 shows an example arrangement of 40 detector modules in a PET scanner. Any number of detector modules can be used within the scope of the disclosed embodiments. The inside numbers in FIG. 1 are the positions of detector modules running counter-clockwise. The outside numbers in FIG. 1 are relative rankings of the timing resolutions of the detector modules. In this example, the detector module with the best timing resolution (rank 1) is paired with (i.e., is placed across from) the detector module with the worst timing resolution (rank 40). The detector module with the second best timing resolution (rank 2) is paired with the detector module with the second worst timing resolution (rank 39).

Figure 2:
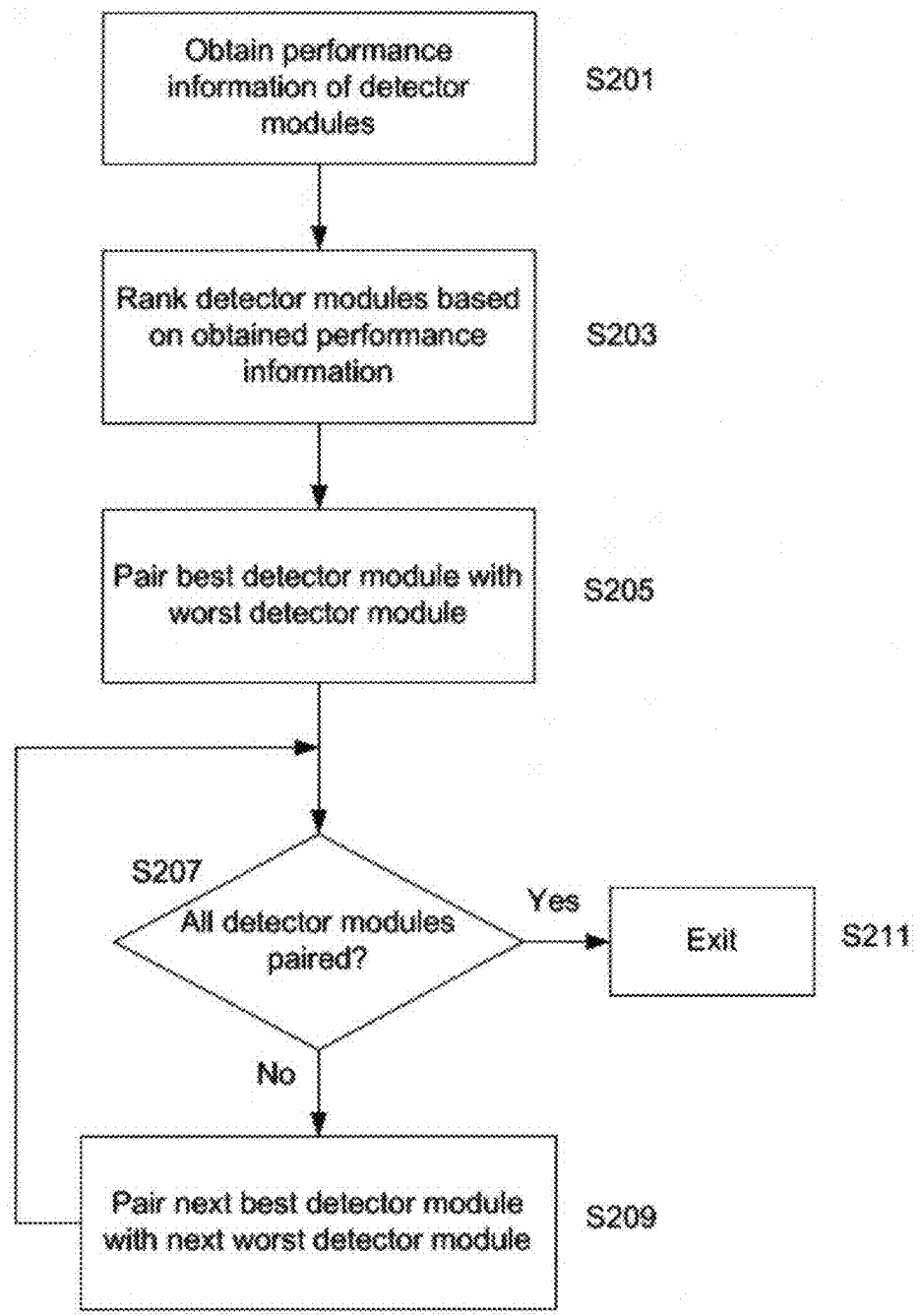
FIG. 2 shows a flowchart of a method of pairing the detector modules based on their performance according to one embodiment.

FIG. 2 shows a flowchart of a method of pairing the detector modules based on their performance according to one embodiment.

In step S201, performance information of the detector modules is obtained. Performance information may include timing resolution, spatial resolution, energy resolution, or other similar performance information of each detector module.

In step S203, the detector modules are ranked based on the obtained performance information.

In step S205, the highest-ranking (best-performing) detector module is paired with the lowest-ranked detector module.

In step S207, the process checks if all detector modules are paired, and if all detector modules are not paired, the next best detector module is paired with the next worst detector module in step S209, and the process goes back to step S207. Otherwise the process exits in step S211.

Alternatively and/or additionally, the detector modules may be paired such that the average timing resolution of each pair is as close to the same as possible.

Alternatively and/or additionally, the detector modules may be paired such that any detector module with a relatively low timing performance has a low probability of being paired with another detector module with a relatively low timing performance.

Figure 3:
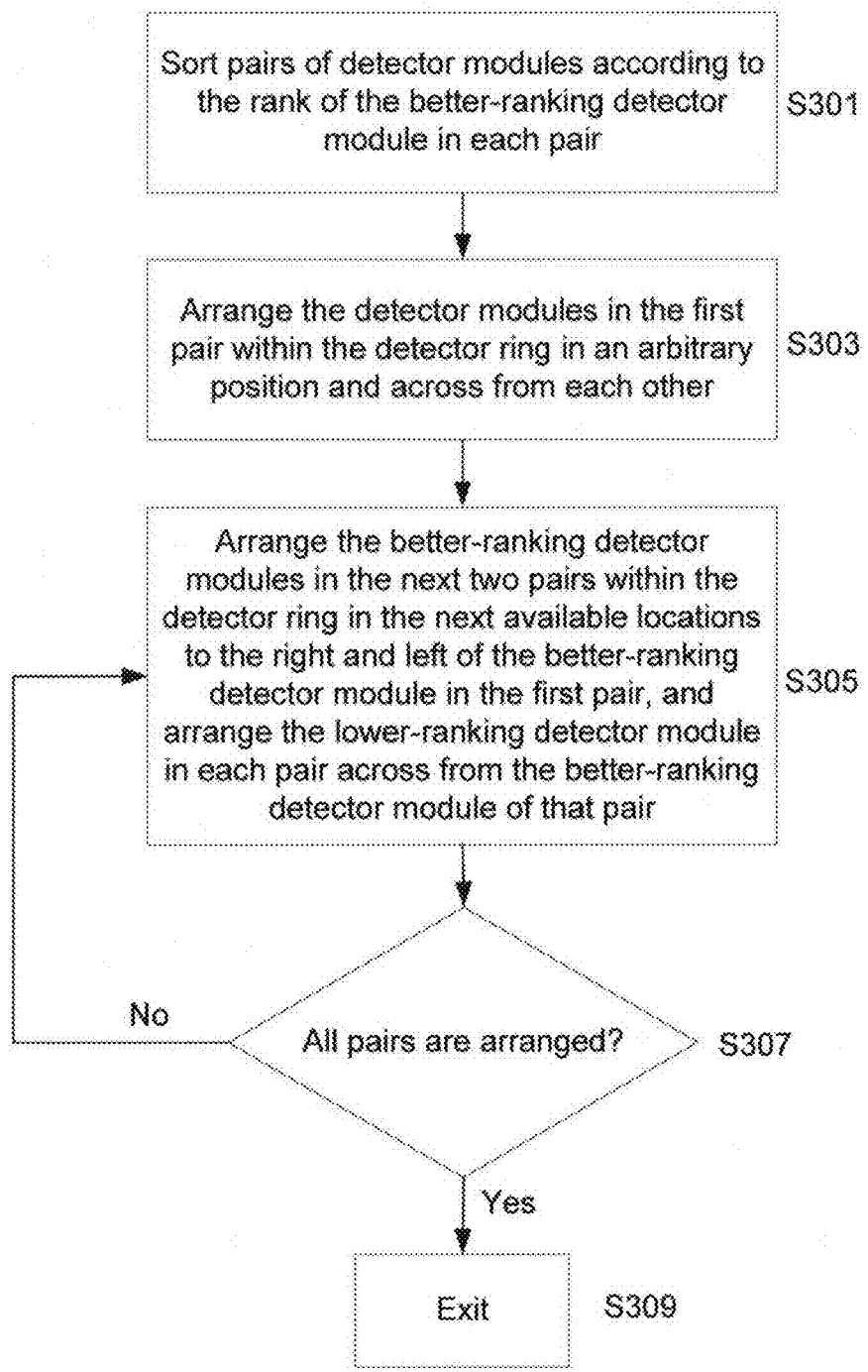
FIG. 3 shows a flowchart of a first method of arranging the detector modules within the scanner ring of a PET scanner according to one embodiment.

FIG. 3 shows a flowchart of a first method of arranging the pairs of detector modules within the scanner ring of a PET scanner according to one embodiment. This embodiment makes the performance more uniform across the FOV. The detector modules may be paired according to any of the above-described embodiments, such as using the method of FIG. 2.

In step S301, the pairs of detector modules are sorted according to the rank of the better-ranking detector module in each pair of detector modules, e.g., the first pair is the pair that includes the best-ranking detector module.

In step S303, the detector modules in the first pair are arranged within the detector ring in an arbitrary position and across from each other.

In step S305, the better-ranking detector modules in the next two pairs are arranged within the detector ring in the next available locations to the right and left of the better-ranking detector in the first pair, and the lower-ranking module in each pair is arranged across from the better-ranking module of that pair.

In step S307, the process checks if all pairs of detector modules are arranged, and if all pairs are not arranged, the process goes back to step S305. Otherwise the process exits in step S309. According to this embodiment, the detector modules belonging to a pair are arranged within a PET scanner such that their locations are the mirror of each other with respect to the center of the FOV.

Figure 4A:
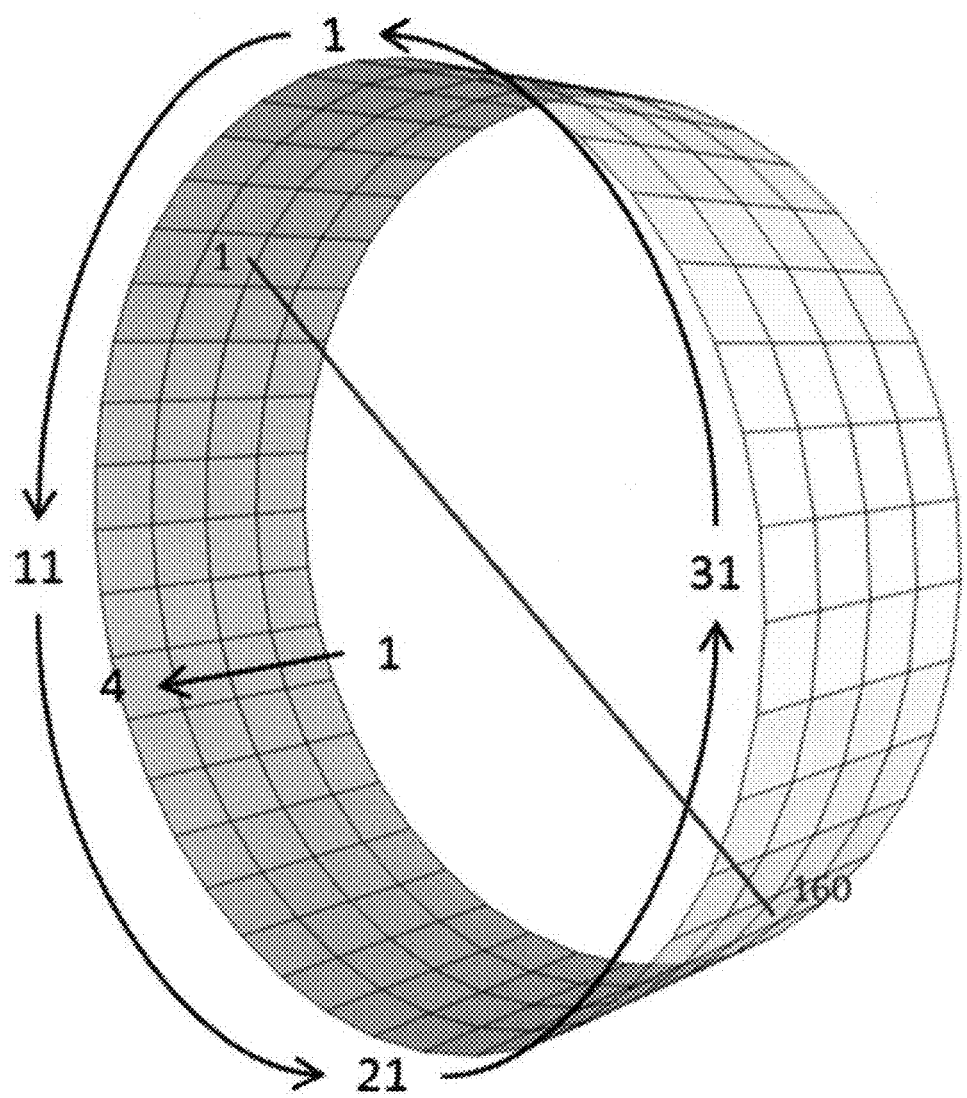
FIGS. 4A and 4B show an example arrangement of 160 detector modules within the scanner ring of a PET scanner.
Figure 4B:
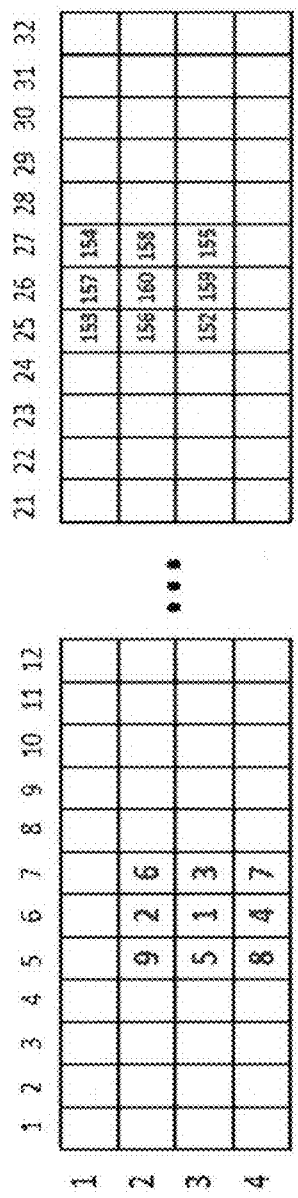

FIGS. 4A and 4B show a 3D and a flattened view of an example arrangement of 160 detector modules within the scanner ring of a PET scanner, respectively. In the example shown in FIGS. 4A and 4B, the detector ring includes multiple detector modules arranged in the axial direction. The detector ring includes 4 detector module locations labeled 1 through 4 in the axial direction, and 40 detector module locations in the azimuthal direction, labeled counterclockwise from 1 through 40. In FIG. 4A, the pair of numbers 1 and 160 connected by a line indicate a pair of detector modules with ranks 1 and 160 arranged across from each other within the detector ring.

Figure 5:
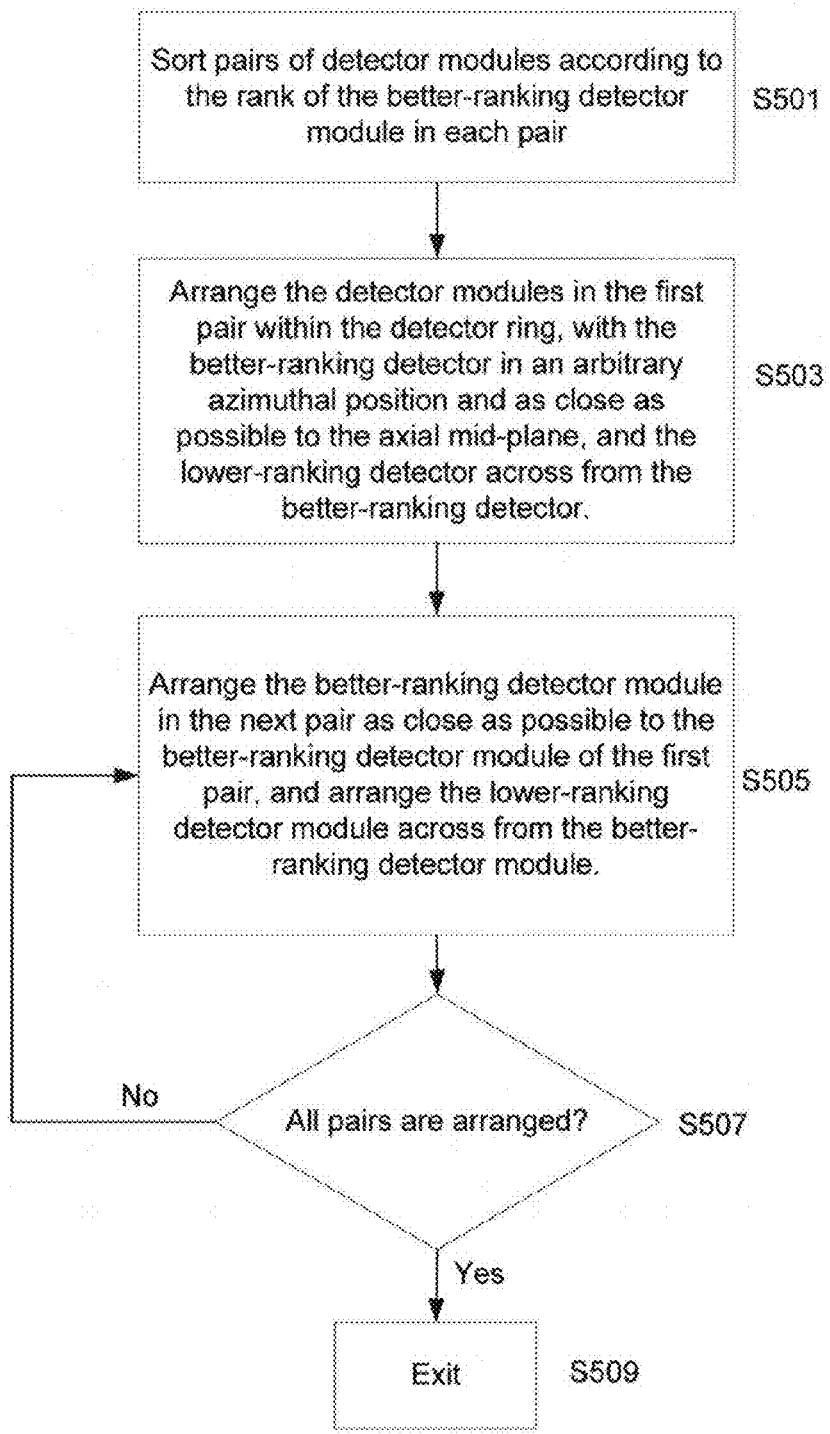
FIG. 5 shows a flowchart of a second method of arranging the detector modules within the scanner ring of a PET scanner according to one embodiment.

FIG. 5 shows a flowchart of a second method of arranging the detector modules within the scanner ring of a PET scanner according to one embodiment. This embodiment makes the performance more uniform across the FOV. The detector modules may be paired according to any of the above-described embodiments.

In step S501, the pairs of detector modules are sorted according to the rank of the better-ranking detector module in each pair of detector modules, e.g., the first pair is the pair that includes the best-ranking detector module.

In step S503, the better-ranking detector module in the first pair is arranged within the detector ring in an arbitrary azimuthal position and as close as possible to the axial midplane, and the lower-ranking detector module in the first pair is arranged across from the better-ranking detector module.

In step S505, the better-ranking detector module in the next pair is arranged within the detector ring as close as possible to the better-ranking detector module of the first pair, and the lower-ranking detector module is arranged across from the better-ranking module.

In step S507, the process checks if all pairs of detector modules are arranged, and if all pairs are not arranged, the process goes back to step S505. Otherwise the process exits in step S509.

Alternatively and/or additionally, an algorithm may be used to consider the line-of-responses (LORs) from the detector modules to optimize the timing resolution uniformity.

Alternatively and/or additionally, the detector modules may be arranged such that an object organ (e.g. the heart) is located in a region with relatively better timing resolution. According to one embodiment, by arranging the detector modules with relatively better performance localized in certain ranges and/or positions, the timing resolution in the FOV becomes non-uniform. In such embodiment, for a task-specific scan (e.g. cardiac imaging or tumor imaging), the object is placed within the region with relatively better timing resolution.

According to one embodiment, the detector modules may be arranged in a PET scanner to equalize timing resolution further based on timing performance of read-out electronics when the readout electronics have non-uniform timing performance. For example, time-to-digital converters (TDCs) implemented in a field-programmable logic array (FPGA) may have different timing accuracy. Timing performance of the read-out electronics may be acquired from previous performance tests for each electronic board, which is usually a standard part of the manufacturing process. According to this embodiment, to equalize the timing performance in a PET system, a detector module with relatively good timing resolution is assembled with readout electronics with relatively poor timing performance to obtain a combined balanced performance. According to this embodiment, performance ranking of a detector module is based on the combined performance of the detector module and the read-out electronics assembled with it during manufacture.

According to one embodiment, the pairs of detector modules are arranged across from each other at arbitrary positions within the detector ring. According to such embodiment, the performance of the LORs which pass near the center of the ring are more uniform.

Figure 6:
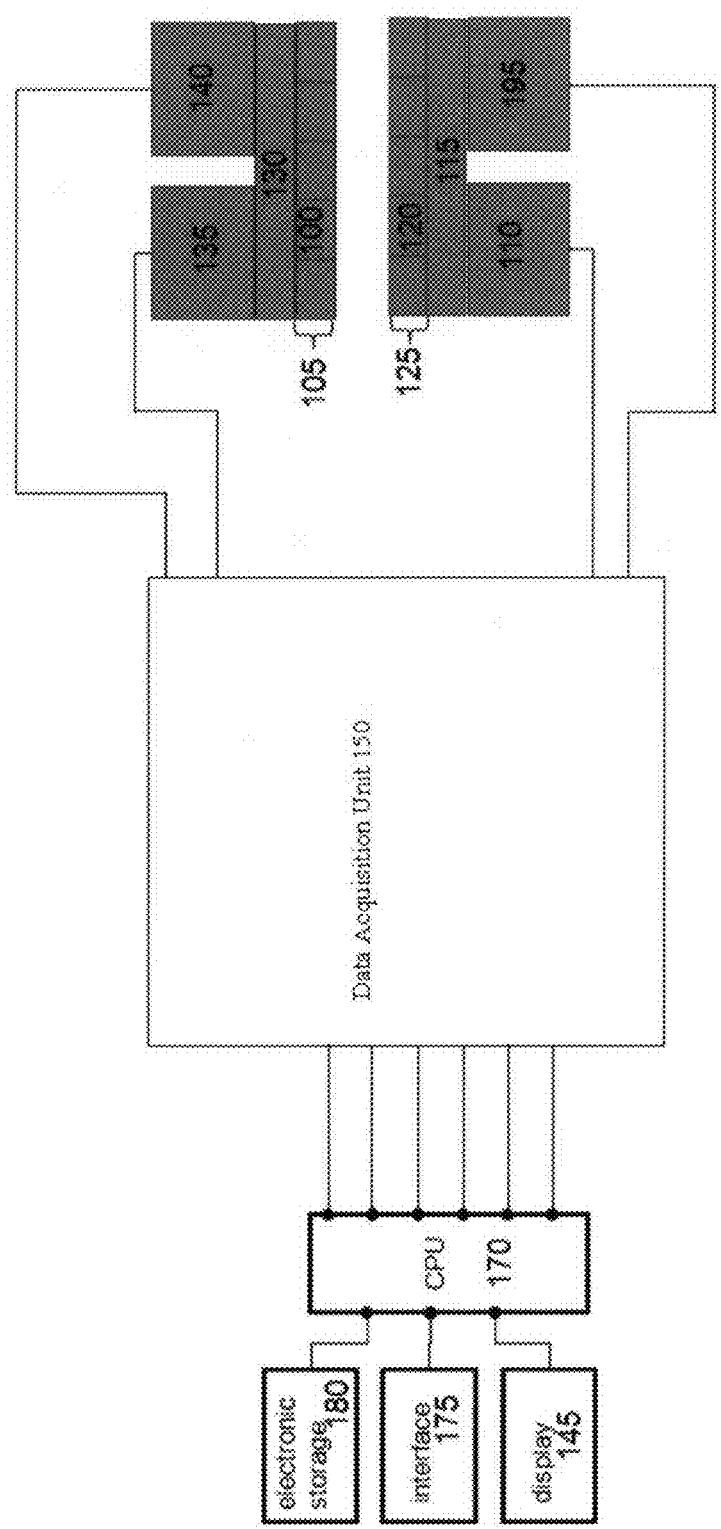
FIG. 6 shows an example block diagram of a gamma ray detector.

FIG. 6 shows an exemplary hardware configuration that can be used with the present technological advancement to detect gamma rays. In FIG. 6, photomultiplier tubes 135 and 140 are arranged over light guide 130, and the array of scintillation crystals 105 is arranged beneath the light guide 130. A second array of scintillation crystals 125 is disposed opposite the scintillation crystals 105 with light guide 115 and photomultiplier tubes 195 and 110 arranged thereover.

In FIG. 6, when gamma rays are emitted from a body under test (not shown), the gamma rays travel in opposite directions, approximately 180° from each other. Gamma ray detection occurs simultaneously at scintillation crystals 100 and 120, and a scintillation event is determined when the gamma rays are detected at scintillation crystals 100 and 120 within a predefined time limit. Thus, the gamma ray timing detection system detects gamma rays simultaneously at scintillation crystals 100 and 120. However, for simplicity only, gamma ray detection is described relative to scintillation crystal 100. One of ordinary skill in the art will recognize, however, that the description given herein with respect to scintillation crystal 100 is equally applicable to gamma ray detection at scintillation crystal 120.

Each photomultiplier tube 110, 135, 140 and 195 is respectively connected to data acquisition unit 150. The data acquisition unit 150 includes hardware configured to process the signals from the photomultiplier tubes. The data acquisition unit 150 measures the arrival time of the gamma ray. The data acquisition unit 150 produces two outputs (one for the combination of PMT 135/140 and one for the combination of PMT 110/195) which encodes the time of the discriminator pulse relative to a system clock (not shown). For a time of flight PET system, the data acquisition unit 150 typically produces a time stamp with an accuracy of 15 to 25 ps. The data acquisition unit measures the amplitude of the signal on each PMT (four of the outputs from data acquisition unit 150).

The data acquisition unit outputs are provided to a CPU, 170, for processing. The processing consists of estimating an energy and position from the data acquisition unit outputs and an arrival time from the time stamps output for each event, and may include the application of many correction steps, based on prior calibrations, to improve the accuracy of the energy, position, and time estimates. As one of ordinary skill in the art would recognize, the CPU 170 can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog or any other hardware description language and the code may be stored in an electronic memory directly within the FPGA or CPLD, or as a separate electronic memory. Further, the electronic memory may be non-volatile, such as ROM, EPROM, EEPROM or FLASH memory. The electronic memory may also be volatile, such as static or dynamic RAM, and a processor, such as a microcontroller or microprocessor, may be provided to manage the electronic memory as well as the interaction between the FPGA or CPLD and the electronic memory.

Alternatively, the CPU 170 may be implemented as a set of computer-readable instructions stored in any of the above-described electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

Once processed by the CPU 170, the processed signals are stored in electronic storage 180, and/or displayed on display 145. As one of ordinary skill in the art would recognize, electronic storage 180 may be a hard disk drive, CD-ROM drive, DVD drive, FLASH drive, RAM, ROM or any other electronic storage known in the art. Display 145 may be implemented as an LCD display, CRT display, plasma display, OLED, LED or any other display known in the art. As such, the descriptions of the electronic storage 180 and the display 145 provided herein are merely exemplary and in no way limit the scope of the present advancements.

FIG. 6 also includes an interface 175 through which the gamma ray detection system interfaces with other external devices and/or a user. For example, interface 175 may be a USB interface, PCMCIA interface, Ethernet interface or any other interface known in the art. Interface 175 may also be wired or wireless and may include a keyboard and/or mouse or other human interface devices known in the art for interacting with a user.

Figure 7:
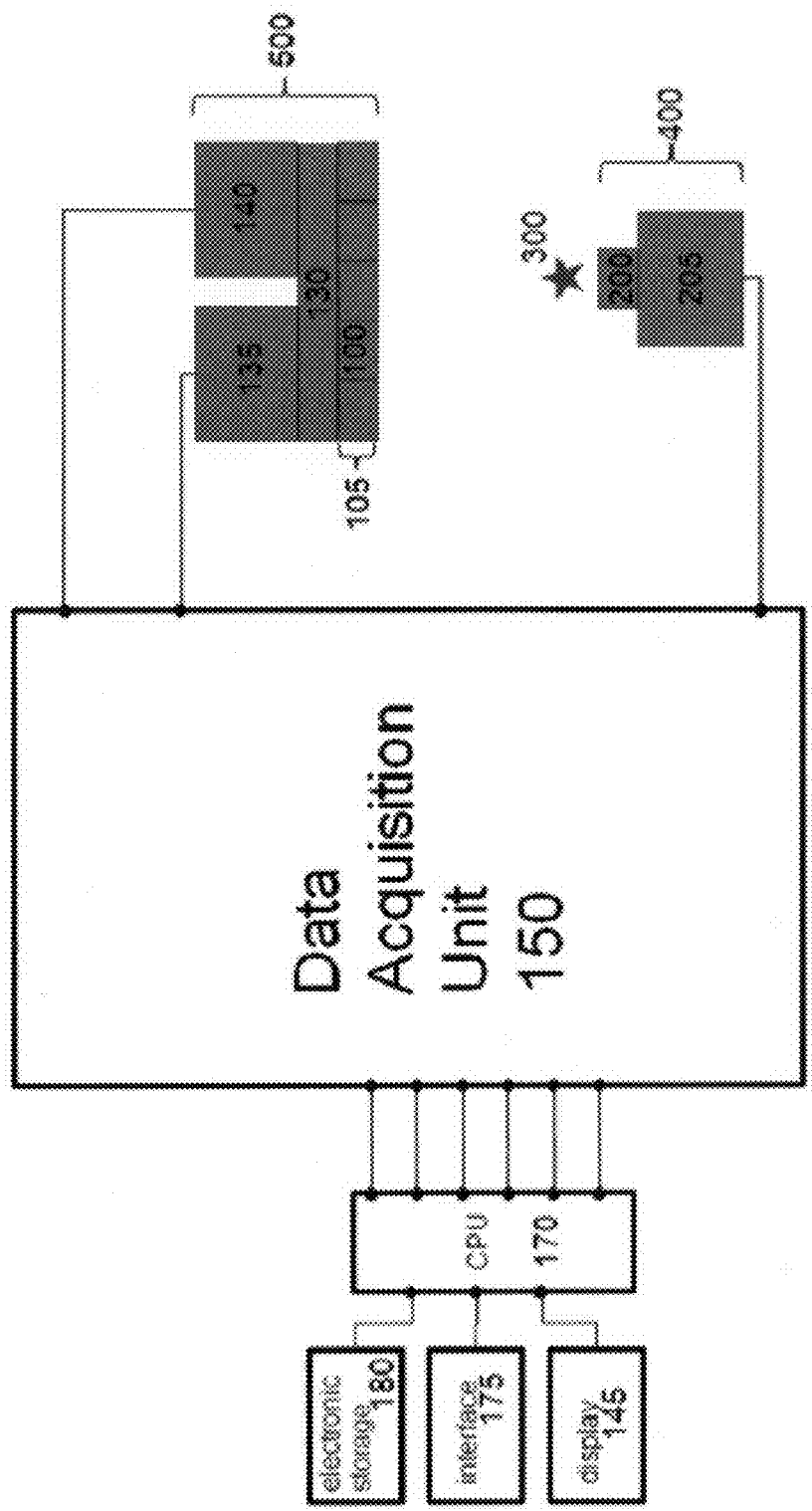
FIG. 7 shows an example block diagram of a modified gamma ray detector used for timing resolution measurement of the detector modules.

FIG. 7 shows an example block diagram of a modified gamma ray detector used for timing resolution measurement of the detector modules. As shown in FIG. 7, a reference detector 400 and a detector under test (DUT) 500 are placed on opposite sides of a radio-isotope source 300 which emits coincident 511 keV gamma rays, such as $^{68}$Ge or $^{22}$Na. The reference detector 400 includes a reference detector scintillator crystal 200 and a reference detector photo-sensor 205.

Figure 8:
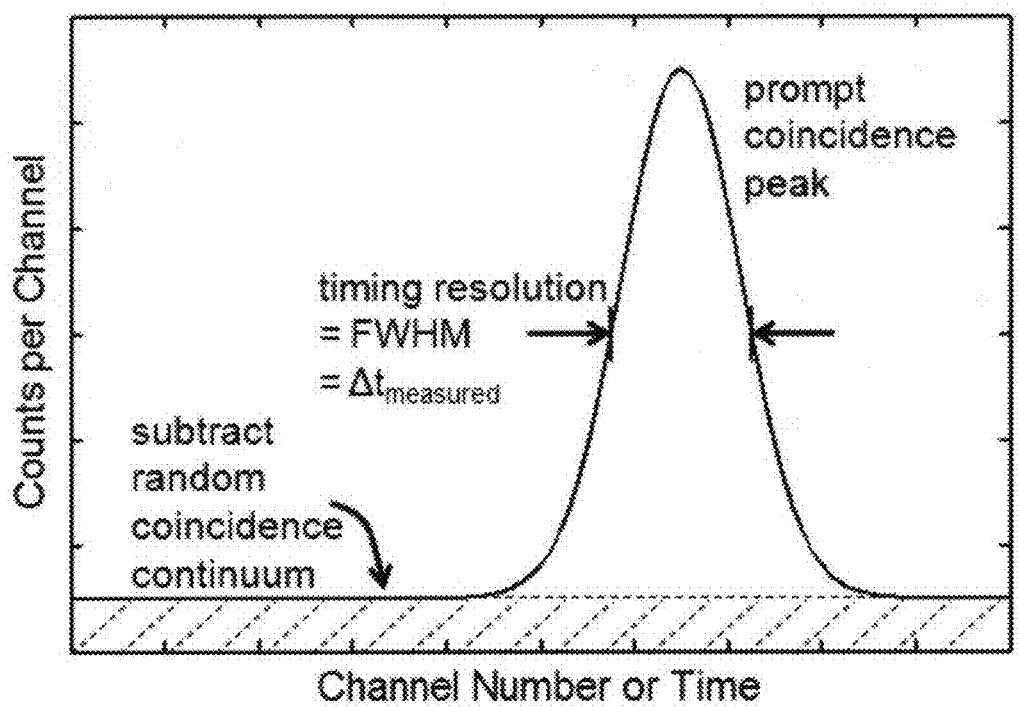
FIG. 8 shows an example timing spectrum of a detector module.

After pairing of the events within a coincidence window by the acquisition system, the timing spectrum will look like FIG. 8. A fraction of the true coincidence events result in gamma rays that are detected nearly simultaneously in both the reference detector 400 and the DUT 500, producing the prompt coincidence peak as shown in FIG. 8. In addition to the coincident events, each detector will also detect single gamma rays where the corresponding gamma ray is not detected by the opposite detector (for example, some gamma rays pass through a detector without interacting). These single gamma rays may be randomly paired by the acquisition system with other single gamma rays in the opposite detector. Since they are not true coincidences, their time distribution is random, resulting in a random coincidence continuum in the timing spectrum as shown in FIG. 8. The measured timing resolution $\Delta t_{measured}$ for the detector pair (i.e. the DUT 500 and the reference detector 400) is equal to the full-width-at-half-maximum (FWHM) of the timing spectrum after subtracting the random coincidence continuum.

Generally, the timing resolutions of each of the individual detectors add in quadrature to produce the measured timing resolution $\Delta t_{measured}$. Accordingly, the timing resolution of the DUT 500 (assuming the timing resolution of the reference detector 400 is known) is given by $$\Delta t_{measured} = \sqrt{(\Delta t_{reference})^2 + (\Delta t_{DUT})^2}$$

$$\Rightarrow \Delta t_{DUT} = \sqrt{(\Delta t_{measured})^2 - (\Delta t_{reference})^2}$$

where $\Delta t_{DUT}$ is the timing resolution of the DUT 500, and $\Delta t_{reference}$ is the timing resolution of the reference detector 400.

Next, a method for prior measurement of the timing resolution of the reference detector 400 is described. According to one embodiment, the reference detector 400 includes a single crystal on a photomultiplier tube, but may alternatively be multi-pixel, in which case the timing resolution of each pixel is determined.

For 3 reference detectors A, B, and C (or more, by extension) with unknown timing resolutions of $\Delta t_A$, $\Delta t_B$, and $\Delta t_C$, the timing resolutions of possible detector pairs, i.e., $\Delta t_{AB}$, $\Delta t_{AC}$, and $\Delta t_{BC}$ are measured. Then, the following set of linear equations (in the least-squares sense, since there is some uncertainty/noise in the measurement) are solved to determine $\Delta t_A$, $\Delta t_B$, and $\Delta t_C$:

$$\begin{bmatrix} 1 & 1 & 0 \\ 1 & 0 & 1 \\ 0 & 1 & 1 \end{bmatrix} \begin{bmatrix} \Delta t_A^2 \\ \Delta t_B^2 \\ \Delta t_C^2 \end{bmatrix} = \begin{bmatrix} \Delta t_{AB}^2 \\ \Delta t_{AC}^2 \\ \Delta t_{BC}^2 \end{bmatrix}$$

Any one of the three reference detectors A, B, or C may be used as the reference detector 400. According to one embodiment, the reference detector with the lowest timing resolution is used.

An alternative method to determine the timing resolution of a reference detector is to build two nominally identical reference detectors (i.e. same type and size of scintillator crystal, same type of reflector around crystal, same optical coupling compound between crystal and PMT, same type of PMT, etc.). The timing resolution of the two nominally identical reference detectors can then be assumed to be identical and given by:

$$\Delta t_{measured} = \sqrt{(\Delta t_{reference})^2 + (\Delta t_{reference})^2} = \sqrt{2 \cdot (\Delta t_{reference})^2} = \sqrt{2} \cdot \Delta t_{reference}$$

$$\Rightarrow \Delta t_{reference} = \frac{\Delta t_{measured}}{\sqrt{2}}$$

Figure 9:
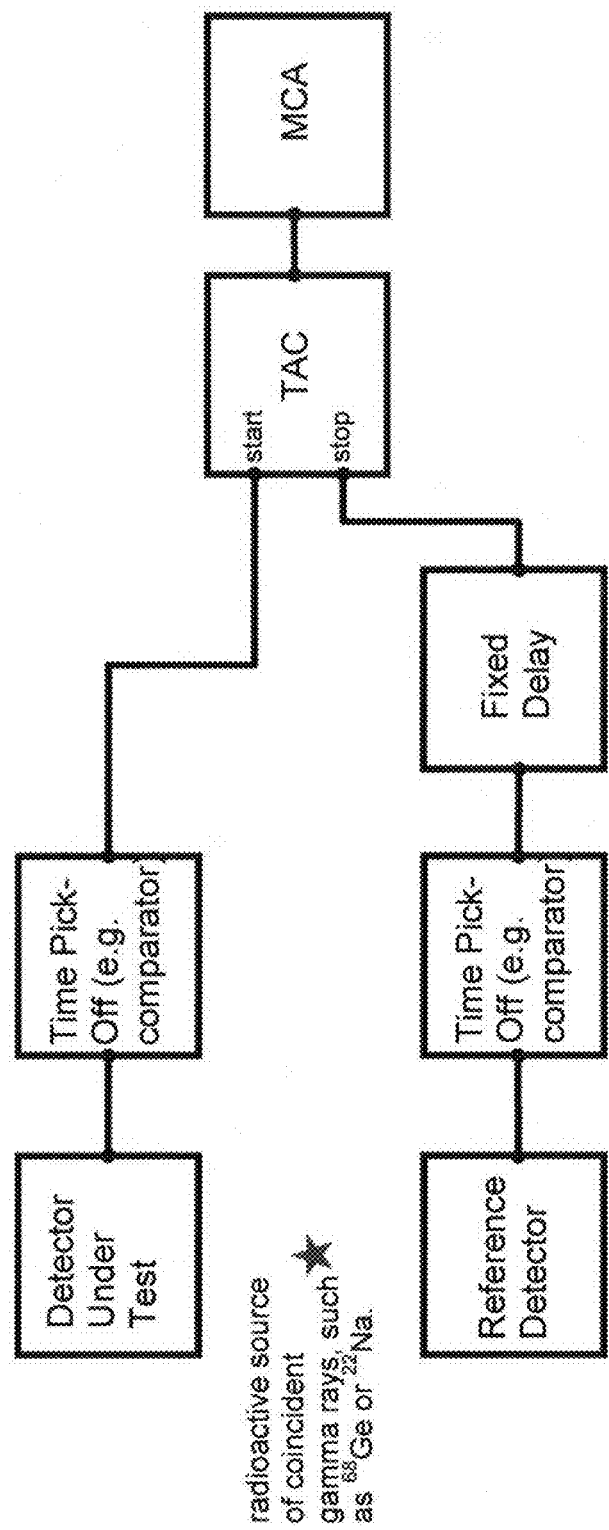
FIG. 9 shows an example block diagram of a first apparatus for timing resolution measurement.

FIG. 9 shows an example block diagram of a first apparatus for timing resolution measurement. A reference detector and a DUT are placed on the opposite sides of a radio-isotope source which emits coincident 511 keV gamma rays, such as $^{68}$Ge or $^{22}$Na. The DUT is connected to a time pick-off module (e.g. a comparator), which is in turn connected to the start input of a time-to-amplitude converter (TAC). The reference detector is connected to a time pick-off module (e.g. a comparator), which is in turn connected to a fixed delay module, and then connected to the stop input of the TAC. The output of the TAC is connected to a multi-channel analyzer (MCA). In FIG. 9, only timing channels are shown. Most measurement systems also record the energy of each event, and often logic circuits are implemented so that only events within a pre-defined energy window are accepted by the MCA.

Figure 10:
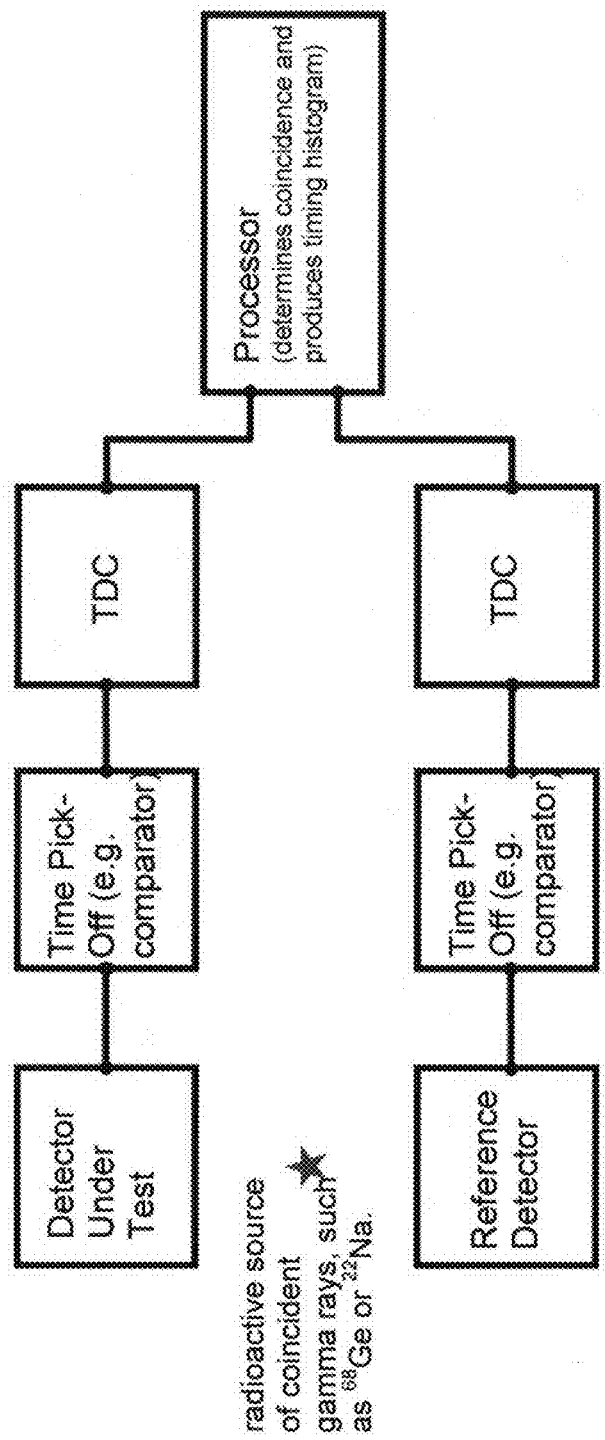
FIG. 10 shows an example block diagram of a second apparatus for timing resolution measurement.

FIG. 10 shows an example block diagram of a second apparatus for timing resolution measurement. A reference detector and a DUT are placed on the opposite sides of a radio-isotope source which emits coincident 511 keV gamma rays, such as $^{68}$Ge or $^{22}$Na. Each of the reference detector and the DUT are connected to a time pick-off module (e.g. a comparator), which is in turn connected to a time-to-digital converter (TDC). Both TDCs are then connected to a processor that determines coincidences and produces a timing histogram. In FIG. 10, only timing channels are shown. Most measurement systems also record the energy of each event, and often only events within a pre-defined energy window are histogrammed by the processor.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions may be executed out of order from that shown or discussed, including substantially concurrently or in reverse order, depending upon the functionality involved, as would be understood by those skilled in the art.

While certain embodiments have been described, these embodiments have been presented by way of example only, and are not intended to limit the scope of the inventions. Indeed, the novel methods, apparatuses and systems described herein may be embodied in a variety of other forms; furthermore, various omissions, substitutions and changes in the form of the methods, apparatuses and systems described herein may be made without departing from the spirit of the inventions. The accompanying claims and their equivalents are intended to cover such forms or modifications as would fall within the scope and spirit of the inventions.

The invention claimed is:

1. A method of determining a relative ordering of detector modules that are configured to be positioned within a predetermined region of a gamma ray detector apparatus, the method comprising:
   obtaining performance information of each of the detector modules; and
   determining the relative ordering of the detector modules within the predetermined region of the gamma ray detector apparatus based on the obtained performance information of the detector modules.

2. The method of claim 1, further comprising:
   arranging the detector modules within the gamma ray detector apparatus based on the determined relative ordering to form a detector ring of the gamma ray detector apparatus.

3. The method of claim 1, wherein the obtaining step comprises:
   obtaining timing resolution information of each of the detector modules.

4. The method of claim 1, wherein the determining step comprises:
   determining the relative location of each of the detector modules so as to at least partially equalize timing resolution across a field of view of the gamma ray detector apparatus.

5. The method of claim 1, wherein each detector module has a corresponding data acquisition device to receive electrical signals, the method further comprising:
   determining performance information of the data acquisition devices,
   wherein the step of determining the relative ordering of each of the detector modules is further based on the performance information of the data acquisition devices.

6. The method of claim 2, wherein
   the determining step further comprises pairing the detector modules into a plurality of pairs of detector modules, based on the obtained performance information; and
   the arranging step further comprises arranging each of the plurality of pairs of detector modules within the detector ring so that each pair of detector modules is located 180 degrees apart from each other along the detector ring.

7. The method of claim 6, wherein
   the determining step further comprises ranking the detector modules based on the performance information; and
   the pairing step comprises pairing the detector modules so that each pair of detector modules has substantially a same average rank.

8. The method of claim 6, wherein the pairing step comprises:

pairing the detector modules such that a probability of pairing two detector modules with a rank lower than a predetermined rank is less than a predetermined threshold.

9. The method of claim 1, wherein the determining step further comprises:
determining the relative ordering of the detector modules based on line of responses from the detector modules such that a timing resolution uniformity of the gamma ray detector apparatus is optimized.

10. A gamma ray detector apparatus, comprising:
a plurality of detector modules arranged to form a detector ring,
wherein the detector modules are arranged by ranking each detector within a predetermined region of the detector ring based on timing resolution information of each of the detector modules, and arranging the detector modules as pairs of detector modules located on opposing sides of the ring, so that each pair has substantially a same average rank.

* * * * *